US011002814B2

(12) United States Patent
Pereira et al.

(10) Patent No.: US 11,002,814 B2
(45) Date of Patent: May 11, 2021

(54) DECODING FROM BRAIN IMAGING DATA OF INDIVIDUAL SUBJECTS BY USING ADDITIONAL IMAGING DATA FROM OTHER SUBJECTS

(71) Applicant: Siemens Medical Solutions USA, Inc., Malvern, PA (US)

(72) Inventors: Francisco Pereira, Jersey City, NJ (US); Ahmet Tuysuzoglu, Franklin Park, NJ (US); Bin Lou, West Windsor, NJ (US); Tommaso Mansi, Plainsboro, NJ (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 251 days.

(21) Appl. No.: 15/793,137

(22) Filed: Oct. 25, 2017

(65) Prior Publication Data

US 2019/0120918 A1      Apr. 25, 2019

(51) Int. Cl.
| | | |
|---|---|---|
| *G01R 33/48* | (2006.01) | |
| *A61B 5/055* | (2006.01) | |
| *A61B 5/00* | (2006.01) | |
| *G06F 3/01* | (2006.01) | |
| *G06T 7/00* | (2017.01) | |
| *G16H 50/70* | (2018.01) | |
| *G06K 9/62* | (2006.01) | |

(52) U.S. Cl.
CPC ........ *G01R 33/4806* (2013.01); *A61B 5/0042* (2013.01); *A61B 5/055* (2013.01); *A61B 5/7267* (2013.01); *A61B 5/0022* (2013.01); *A61B 5/4064* (2013.01); *A61B 5/7246* (2013.01); *A61B 5/7264* (2013.01); *A61B 2576/026* (2013.01); *G06F 3/015* (2013.01); *G06K 9/6247* (2013.01); *G06K 9/6269* (2013.01); *G06K 2209/05* (2013.01); *G06T 7/0012* (2013.01); *G06T 2207/20081* (2013.01); *G16H 50/70* (2018.01)

(58) Field of Classification Search
CPC ..... G06T 7/0012; G06T 7/143; A61B 5/4064; A61B 5/0042
See application file for complete search history.

(56) References Cited

PUBLICATIONS

Pereira et al., "Machine learning classifiers and fMRI: a tutorial overview", NeuroImage, vol. 45, Issue 1, Supplement 1, Mar. 2009, pp. S199-S209. (Year: 2009).*

(Continued)

*Primary Examiner* — Amanda Lauritzen Moher
*Assistant Examiner* — Jillian K. McGough

(57) ABSTRACT

A computer-implemented method for decoding brain imaging data of individual subjects by using additional imaging data from other subjects includes receiving a plurality of functional Magnetic Resonance Imaging (fMRI) datasets corresponding to a plurality of subjects. Each fMRI dataset corresponds to a distinct subject and comprises brain activation patterns resulting from presentation of a plurality of stimuli to the distinct subject. A group dimensionality reduction (GDR) technique is applied to the example fMRI datasets to yield a low-dimensional space of response variables shared by the plurality of subjects. A model is trained to predict a set of target variables based on the low-dimensional space of response variables shared by all subjects, wherein the set of target variables comprise one or more characteristics of the plurality of stimuli.

11 Claims, 12 Drawing Sheets

(56) References Cited

PUBLICATIONS

Rustandi et al., "Integrating multiple-study multiple-subject fMRI datasets using canonical correlation analysis", Proc. MICCAI 2009 Workshop: Statist. Model. Detection Issues in Intra- and Inter-Subject Functional MRI Data Anal., Sep. 2009 (Year: 2009).*

Sona et al., "Inferring Cognition from fMRI Brain images", Artificial Neural Networks—ICANN 2007. ICANN 2007. Lecture Notes in Computer Science, vol. 4669. Springer, Berlin, Heidelberg (2007). (Year: 2007).*

Cohen et al., "Computational approaches to fMRI analysis", Nat Neurosci. Feb. 23, 2017; 20(3): 304-313. (Year: 2017).*

Turek et al., "A semi-supervised method for multi-subject FMRI functional alignment", 2017 IEEE International Conference on Acoustics, Speech and Signal Processing (ICASSP), New Orleans, LA, Mar. 2017, pp. 1098-1102. (Year: 2017).*

Hintz, J.J., "Generative Adversarial Reservoirs for Natural Video Prediction", University of Texas (UT) Electronic Theses and Dissertations, Dec. 2016. (Year: 2016).*

Xu et al., "Computer-generated fMRI phantoms with motion-distortion interaction", Magnetic Resonance Imaging 25 (2007) 1376-1384. (Year: 2007).*

Anderson et al., "Enabling factor analysis on thousand-subject neuroimaging datasets," 2016 IEEE International Conference on Big Data (Big Data), Washington, DC, 2016, pp. 1151-1160, doi: 10.1109/BigData.2016.7840719. (Year: 2016).*

Vodrahalli et al. "A Semantic Shared Response Model". ICML Workshop on Multi-view Representation Learning , Jun. 2016. Oral Presentation and Poster. (Year: 2016).*

Mouzon G., Operational methods and models for minimization of energy consumption in a manufacturing environment, PhD thesis, Wichita State University, (2008).

Zhu, J. Y., Park, T., Isola, P., & Efros, A. A. (2017). Unpaired image-to-image translation using cycle-consistent adversarial networks.

Capros P., EU energy trends 2030, Directorate General for Energy, European Commission, 2009 (update 2013).

Gutowski T., et al. Environmentally benign manufacturing: observations from Japan, Europe and the United States, Journal of Cleaner Production, 13, pp. 1-17, 2005.

Fysikopoulos A. et al., Energy efficiency of manufacturing processes: a critical review, Procedia: CIRP—46th Conference on Manufacturing Systems, pp. 628-633, 2013.

Munoz A.A., and Sheng P., A analytical approach for determining the environmental impact of machining processes, Journal of Materials Processing Technology, 53, 1995.

He Y, et al., Analysis and estimation of energy consumption for numerical contron machining, Journal of Engineering Manufacturing, 226, pp. 255-266, 2012.

Garey and Johnson Computers and intractability: a guide to the theory of NP-completeness, W.H. Preeman and Company, NY, 1979.

Bengio, Y., Courville, A.C., Goodfellow, I.J., Mirza, M., Ozair, S., Pouget-Abadie, J., Warde-Farley, D., & Xu, B. (2014). Generative Adversarial Nets. NIPS.

Radford et. al., Unsupervised Representation Learning with Deep Convolutional Generative Adversarial Networks; ICLR; 2016.

Arjovsky et. al., Wasserstein GAN; 2017.

* cited by examiner

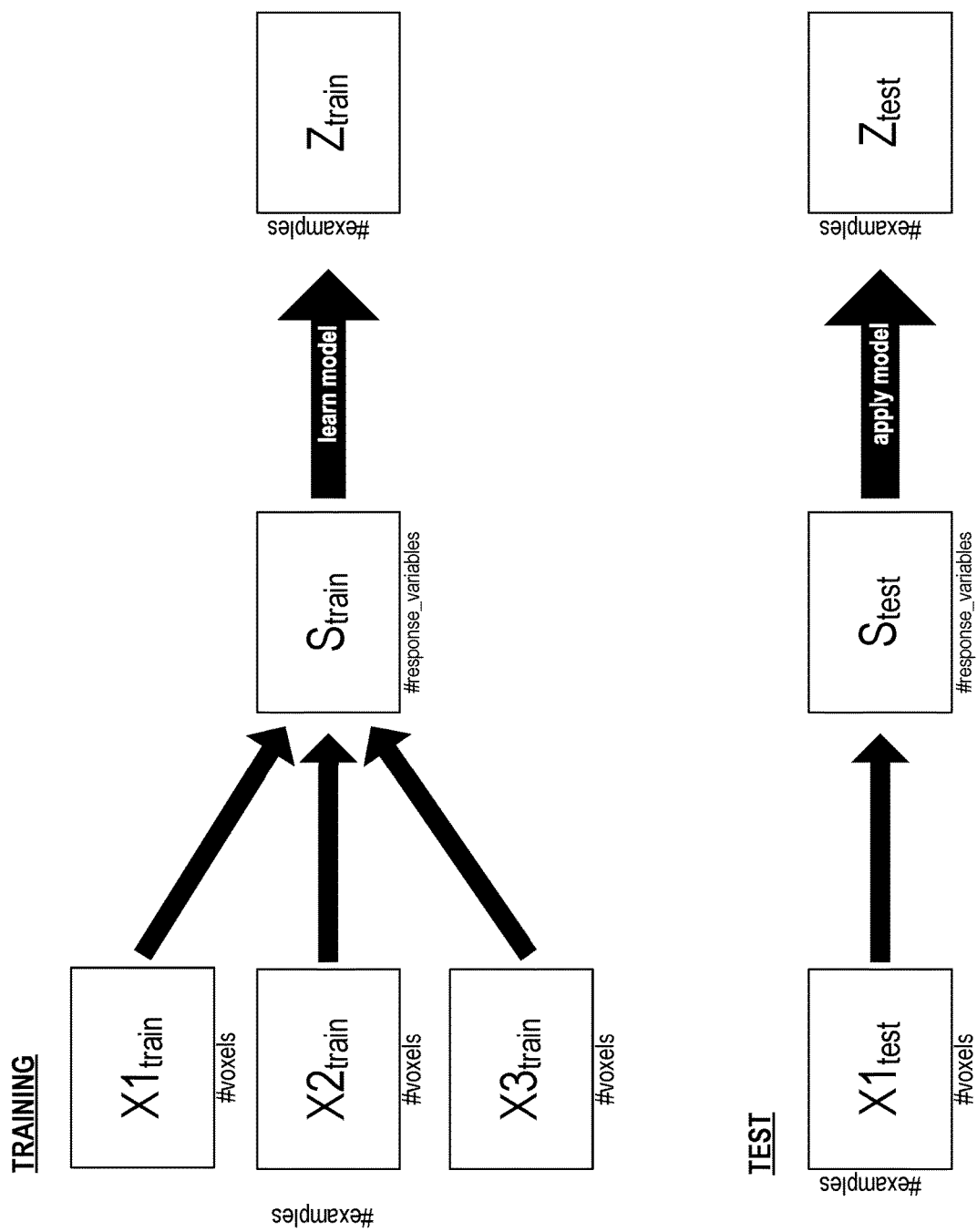

DECODING FROM BRAIN IMAGING DATA OF INDIVIDUAL SUBJECTS BY USING ADDITIONAL IMAGING DATA FROM OTHER SUBJECTS

GOVERNMENT INTERESTS

This invention was made with government support under grant FA8650-14-C-7358 awarded by Air Force Research Laboratory. The government has certain rights in the invention.

This research is based upon work supported in part by the Office of the Director of National Intelligence (ODNI), Intelligence Advanced Research Projects Activity (IARPA), via Air Force Research Laboratory (AFRL). The views and conclusions contained herein are those of the authors and should not be interpreted as necessarily representing the official policies or endorsements, either expressed or implied, of ODNI, IARPA, AFRL, or the U.S. Government. The U.S. Government is authorized to reproduce and distribute reprints for Governmental purposes notwithstanding any copyright annotation thereon.

TECHNICAL FIELD

The present invention relates generally to methods, systems, and apparatuses for improving decoding from brain imaging data of individual subjects by using additional imaging data from other subjects. The technology described herein may be applied, for example, to answering clinical questions based on magnetic resonance imaging data.

BACKGROUND

State-of-the-art functional MRI (fMRI) experiments often use complex stimuli, with the ultimate goal being to identify what in the brain activation encodes characteristics of those stimuli (e.g., visual, semantic, etc.). This is often done by learning a mapping that associates the presence of each characteristic with its effect on the pattern of brain activation across voxels. This is then used to decode those features from new brain imaging data. The mapping is learned with data for a single subject, and works only on that subject. Any general conclusion about stimulus representations can only be drawn by comparing, post-hoc, the brain regions associated with each characteristic, across subjects. Furthermore, functional MRI data are very noisy, so it may be difficult to learn the mapping for certain subjects.

Conventional approaches rely on there being multiple subjects on whom corresponding fMRI datasets—using the same stimuli—were acquired. For example, one conventional technique averages data from multiple subjects. This requires first aligning subjects based on their anatomical scans—with any registration technique—and then applying the same transformation to functional imaging data, averaging the resulting transformed data across subjects. This reduces noise but destroys any fMRI activation that is not focal and does not overlap across people. This is an issue because it is already known that information resides in the overall distributed pattern of brain activation, rather than just in specific locations. A second conventional technique combines data from multiple subjects into a single representation using a group dimensionality reduction method. This is effective but means that all subjects must be available for use at both the time we learn the mapping learning and the time we use it for testing; any results obtained pertain to the group, rather than individual subjects.

SUMMARY

Embodiments of the present invention address and overcome one or more of the above shortcomings and drawbacks by providing methods, systems, and apparatuses related to improving decoding from brain imaging data of individual subjects by using additional imaging data from other subjects.

According to some embodiments, a computer-implemented method for decoding from brain imaging data of individual subjects by using additional imaging data from other subjects includes receiving a plurality of functional Magnetic Resonance Imaging (fMRI) datasets corresponding to a plurality of subjects. Each fMRI dataset corresponds to a distinct subject and comprises patterns brain activation resulting from presentation of a plurality of stimuli to the distinct subject. A group dimensionality reduction (GDR) technique is applied to the example fMRI datasets to yield a low-dimensional space of response variables shared by the plurality of subjects. A model (e.g., a Recurrent Neural Network) is trained to predict a set of target variables based on the low-dimensional space of response variables shared by all subjects. The set of target variables comprise one or more characteristics of the plurality of stimuli. Once the model is trained, it can be applied to new fMRI datasets corresponding to new patients by first applying the GDR technique to transform the new fMRI dataset into the low-dimensional space and then applying the model to predict one target variable.

Various enhancements, refinements, and other modifications may be made to the aforementioned method in different embodiments. For example, the GDR technique used in the aforementioned method may be Shared Response Modelling, Canonical Correlation Analysis, or a supervised Shared Response Modelling technique that combines application of the GDR technique to the example fMRI datasets and training of the model. The characteristics in the target variables may include, for example, a visual representation of one or more stimulus included in the plurality of stimuli or a semantic representation of one or more stimulus included in the plurality of stimuli. In some embodiments, at least a portion of the plurality of fMRI datasets comprise synthetic datasets. In these embodiments, the synthetic datasets may be generated using a Generative Adversarial Network (GAN) framework comprising a generator, a discriminator, and a semantic decoder network, wherein the generator evolves with gradients back-propagated from the semantic decoder network and the discriminator. In other embodiments, the synthetic datasets are generated using a GAN framework comprising a generator and a discriminator connected using a cyclic consistency constraint that minimizes the difference between the plurality of stimuli and generated stimuli produced by the generator.

According to another aspect of the present invention, as described in some embodiments, a second computer-implemented method for decoding from brain imaging data of individual subjects by using additional imaging data from other subjects includes receiving a first set of fMRI datasets corresponding to a plurality of subjects, wherein (a) each fMRI dataset corresponds to a distinct subject; (b) each fMRI dataset comprises patterns brain activation resulting from presentation of a plurality of stimuli to the distinct subject, (c) each fMRI data is in voxel space. A GDR technique is applied to the first set of fMRI datasets to yield a low-dimensional space of response variables shared by the plurality of subjects. A second set of fMRI datasets corresponding to the plurality of subjects is generated by projecting the low-dimensional space of response variables back to voxel space. Then a model is trained to predict a set of target variables based on the second set of fMRI datasets, wherein the set of target variables comprise one or more characteristics of the plurality of stimuli. To apply this model to a new fMRI dataset corresponding to a new subject, the GDR technique is first applied to transform the new fMRI dataset into new response variables in the low-dimensional space. Next, the low-dimensional space of response variables are projected back to voxel space; and the model to predict one or more target variables. The various features and enhancements discussed above with respect to the first method may be similarly applied to this second method for decoding from brain imaging data.

In other embodiments, a system for decoding from brain imaging data of individual subjects by using additional imaging data from other subjects an fMRI scanner and one or more processors. The fMRI scanner is configured to acquire an fMRI dataset corresponding to a subject. This fMRI dataset comprises brain activation patterns resulting from presentation of a plurality of stimuli to the distinct subject. The processors are configured to apply a group dimensionality reduction (GDR) technique to the fMRI dataset to transform it into a low-dimensional space of response variables shared by a plurality of subjects. The processors apply a machine learning model to the transformed fMRI dataset to predict one or more target variables.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawing exemplary embodiments that are presently preferred, it being understood, however, that the invention is not limited to the specific instrumentalities disclosed. Included in the drawings are the following figures:

FIG. 3A shows how multi-subject dimensionality reduction may be used to enhance the training and test process, according to some embodiments;

DETAILED DESCRIPTION

The following disclosure describes the present invention according to several embodiments directed at methods, systems, and apparatuses related to improving decoding from brain imaging data of individual subjects by using additional imaging data from other subjects. The techniques described herein are important for the purpose of improving the performance of brain decoding systems beyond what would be feasible with the functional MRI data from a single subject. These techniques can also be used for denoising by re-representing the data from a subject to only contain the information explained by latent variables. A second important aspect is that it allows for data from multiple subjects to be used in building better models at one point in time (e.g., by an imaging company) and used much later to improve decoding on a new subject (e.g., by an end user).

Figure 1:
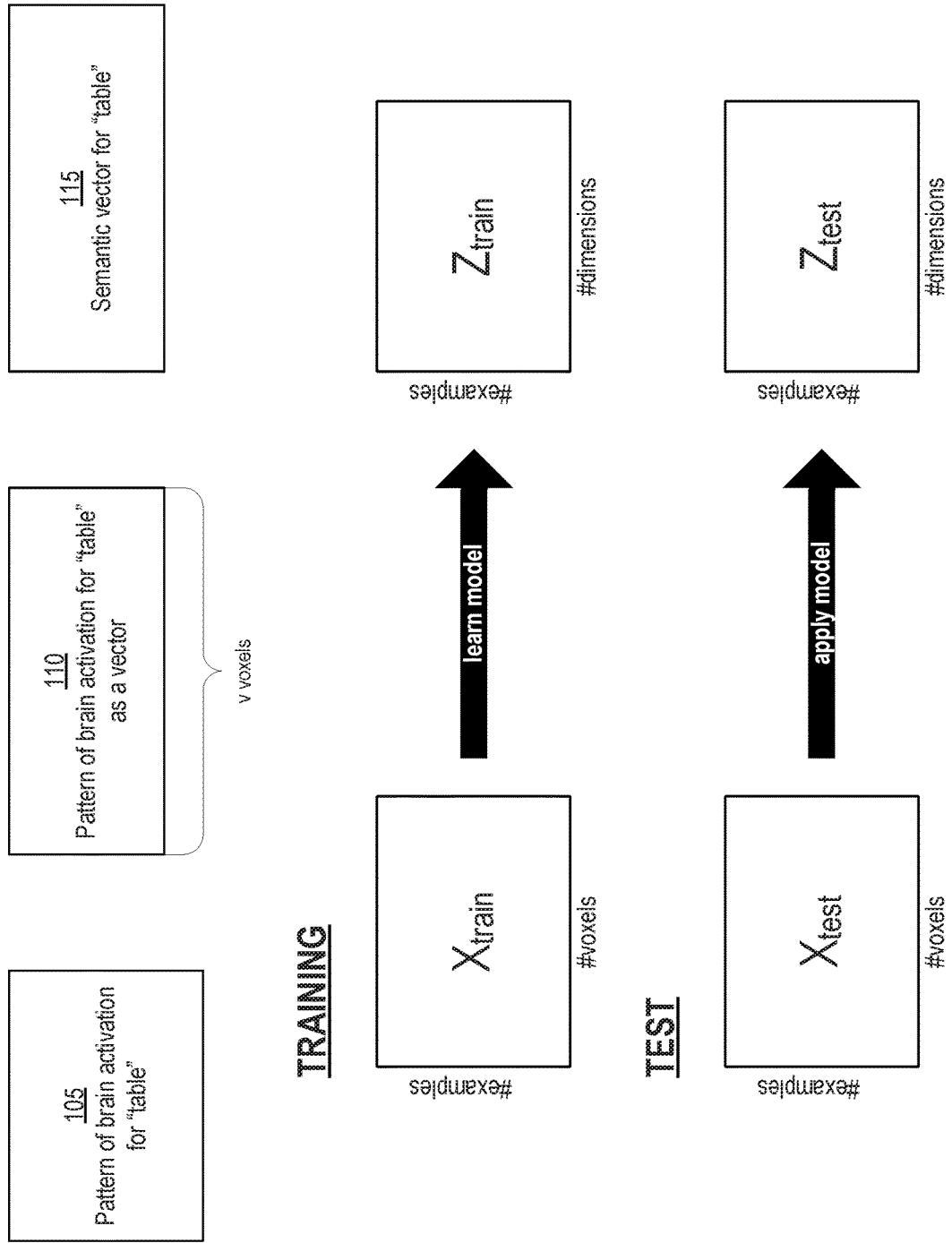
FIG. 1 illustrates the decoding setting, according to some embodiments.

FIG. 1 illustrates the decoding setting, according to some embodiments. In this example, the subject has been presented the concept of a "table." Using fMRI, a pattern of brain activation 105 is acquired. This pattern of brain activation 105 is converted into a vector 110 with one value per voxel. The concept of "table" also has an associated semantic vector 115 in this example.

The patterns of activation for many concepts can be assembled into a matrix, with one pattern per row; a corresponding matrix can be created for the respective semantic vectors. In this setting, one may learn a decoding model M that predicts a set of target variables Y (characteristics) from fMRI data $X_{train}$, so $$Z_{train} = M(X_{train}).$$

Additionally, the values of target variables Y (characteristics) may be predicted from imaging data $X_{test}$, so $$Z_{test} = M(X_{test}).$$

According to some embodiments, two different approaches are used for using data from multiple subjects to improve decoding in test data from a single subject: dimensionality reduction and denoising. The techniques described herein utilize a group dimensionality reduction (GDR) technique (e.g., Shared Response Modelling, SRM, or generalized Canonical Correlation Analysis, gCCA) which learns to decode brain activation in each subject as a combination of common, shared responses. In the GDR setting, the aim is to achieve functional alignment of stimuli responses in distinct subjects assuming that the stimuli invoke similar functional responses. Essentially, GDR maps the activation across the subject's voxels to a new space that is shared between the subjects.

Figure 2:
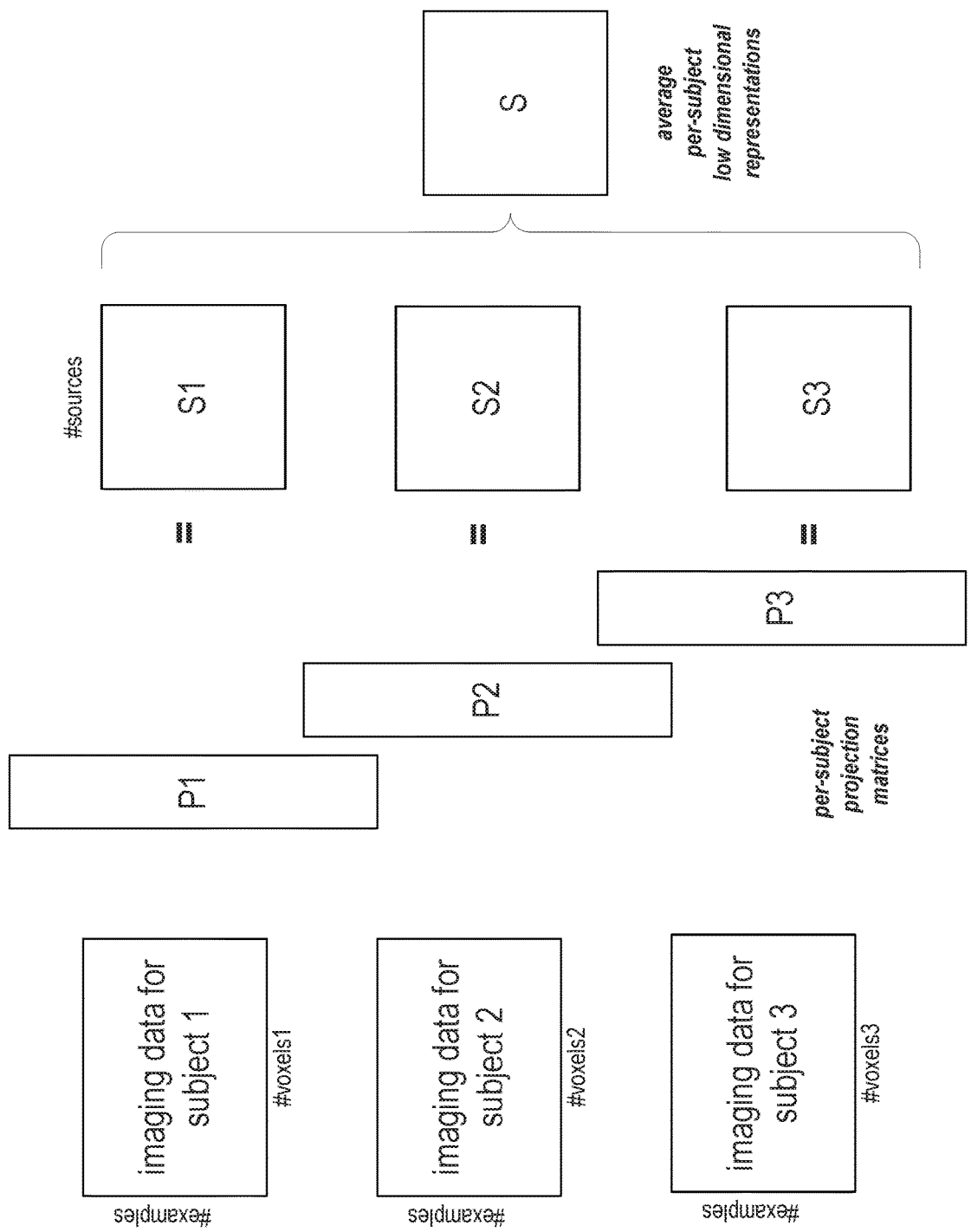
FIG. 2 illustrates how the imaging data for a plurality of subjects can be processed into average per-subject low dimensional representations of the data.

FIG. 2 illustrates how the imaging data for a plurality of subjects can be processed into average per-subject low dimensional representations of the data. In this example, a per-subject project matrix is applied to the imaging data for each subject to yield the low dimensional representations of the subject's data. For example, in FIG. 2, projection matrix P1 is applied to the imaging data from subject 1 to yield low dimensional representation S1, P2 is applied to imaging data from subject 2 to yield low dimensional representation S2, etc. Then, the low dimensional representations from each subject are averaged to yield the average per-subject low dimensional representations for the population (represented in FIG. 2 as S).

The example of FIG. 2 assumes that the response of each voxel to the range of stimuli is a combination of a small number of response variables, which represent characteristics of the stimuli. Additionally, this assumes that these response variables are present in all the subjects (if they all respond in the same way) and that the activation that is not being driven by the common response variables is irrelevant. The mapping can then be learned from these common variables, rather than voxels; it can then be applied to a similar transformation of new test data, not used to fit the model, on which decoding is to be performed.

Figure 3B:
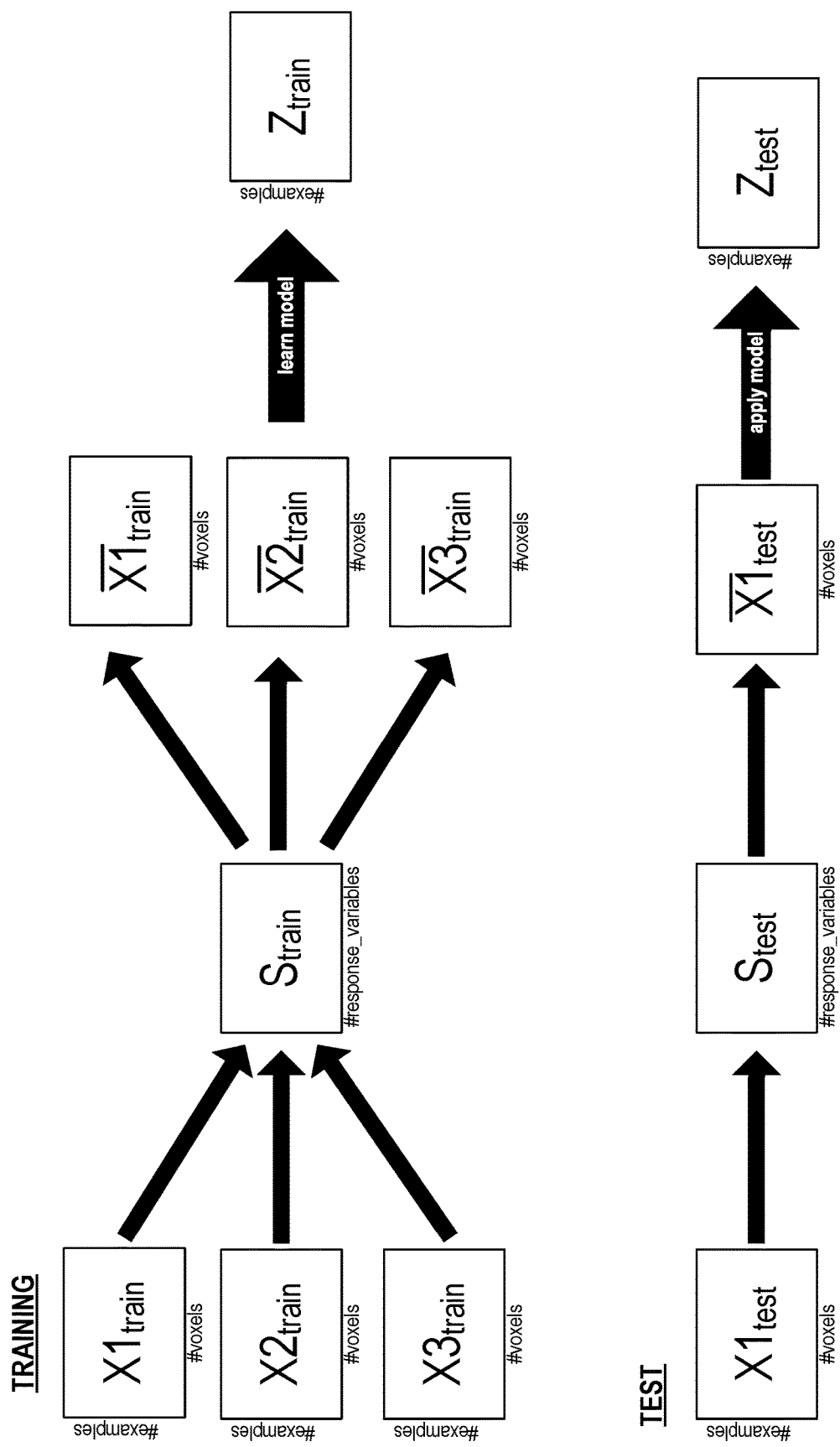
FIG. 3B shows how multi-subject denoising may be used to enhance the training and test process, according to some embodiments.

FIGS. 3A and 3B show two options for modifying the training and test procedure with a single subject. FIG. 3A shows how multi-subject dimensionality reduction may be used enhance the training and test process, according to some embodiments. Using a GDR technique, training data from each subject is transformed into a low-dimensional space of response variables shared by all subjects $S_{train}$. The decoding model is trained on these response variables $S_{train}$ to produce $Z_{train}$. This is illustrated in the top section of FIG. 3A. The transformation learned there is applied to the test data of the individual subject, and the decoding model applied to the resulting response variables. This is illustrated in the bottom of FIG. 3A.

FIG. 3B shows how multi-subject denoising may be used to enhance the training and test process, according to some embodiments. The training data from each subject is transformed into a low-dimensional space of response variables shared by all subjects $S_{train}$ using GDR. The training data is then transformed back into the original space, stripped of all activation that is not explained by the common response variables (denoted by $\overline{X1}_{train}$, $\overline{X2}_{train}$, and $\overline{X3}_{train}$ in FIG. 3B). This is then used to learn the decoding model M, as illustrated in top portion of FIG. 3B. The same transformation to and from the low-dimensional space is applied to the test data of the individual subject, and the decoding model applied to this, as illustrated in the bottom of FIG. 3B.

The input to a GDR is a matrix $X_{train\_i}$ for each subject i, with #examples rows (time points, stimuli) and #voxels_i columns. GDRs allow the data of each subject to be transformed from #time points x #voxels to #time points x #response variables, where the latter is shared by all subjects. GDR may then be formulated as follows:

$$S_i = T_i(X\text{train}_i),$$

where $S_i$ is the representation of the subject i's stimuli imaging data in the aligned functional space. $T_i$ is the projection operator that performs the mapping from the voxel space to the shared voxel space. For the purposes of generality, it may be assumed that this transformation operation is subject-specific however it can also accommodate a common projector. This transformation can be inverted through the use of an operator to yield a reconstruction transformation $W_i$, i.e.

$$\hat{X}_{train_i} = W_i S_i.$$

The techniques described herein rely on deriving a common representation S from all subject datasets $X_{train_i}$ which correspond across subjects who all saw the same stimuli, as $$S = \sum_{i=1}^{m} S_i$$

from the representations $S_i$ of individual subjects. As described earlier, the decoding setting is one where a machine learning model M is learned that predicts a set of target variables Z from imaging data $X_{train}$, thus $$Z = M(X_{train})$$

and the values of target variables Y are predicted from imaging data $X_{test}$:

$$\hat{Z} = M(X_{test}).$$

The GDR can be learned from all datasets available for multiple subjects, as described above, yielding a common representation S and transformations $T_i/W_i$ for each subject. The denoised dataset for each subject is obtained by applying the reconstruction transformation to the common representation that yields $\hat{X}_{train_i}$. This is then used to learn the decoding model M in each person from a cleaned version of their data $$Z = M(\hat{X}_{train_i}).$$

At test time, the dataset for each subject is projected to the common space and reconstructed using only the information that survives that projection, yielding $$\hat{Z} = M(W_i(T_i(X_{test_i}))).$$

The GDR can be learned from all datasets available for multiple subjects, as described above, yielding a common representation S and transformations $T_i/W_i$ for each subject. In this case, the prediction model is learned from the common representation S, so $$Z = M(S).$$

At test time, the dataset for each subject is projected to the common space, and the prediction generated using only the information that survives that projection, yielding $$\hat{Z} = M(T_i(X_{test_i})).$$

In both approaches, it is also possible to collect the training data for a new subject after the GDR is learned, as long as the same stimuli are used. The transformations $T_i$ and $W_i$ can then be derived with respect to the common representation S learned from all the existing subjects.

The subject specific representations are usually obtained through an optimization framework that combines problem elements that are deemed significant such as the combination of fidelity to the voxel data and shared response space. Perhaps one of the most straightforward ways of finding a shared response is to borrow elements from non-negative matrix factorization literature. Although activation data is not constrained to be positive, other forms of regularization can be used to enforce commonality across distinct subjects. One representative technique from this class of method is the shared response model (SRM) that aims to find a common response by finding orthogonal image spaces for each subject:

$$\operatorname*{argmin}_{W_i S} \sum_{i=1}^{N} \|X_i - SW_i\|$$

$$\text{s.t. } W_i W_i^T = I$$

where S is the shared activation matrix and $W_i$ encodes orthogonal image spaces for each subject.

In SRM, the degree of freedom is given to each subject in selecting its orthogonal image spaces. Given $W_i$, it is then trivial to find the representation of the subject in the shared space:

$$S_i = X_i W_i^T,$$

where $S_i$ can be used in subsequent learning tasks. A de-noised representation in the voxel space can be obtained as follows:

$$\hat{X}_i = S_i W_i.$$

Because S is shared across all the subjects, it can be regarded as the activation matrix of a super subject.

Other ways of using matrix factorization techniques can be devised to incorporate other forms of regularization such as box constraints on S. An alternative approach to finding representations in a shared space across subjects can be achieved through by extracting highly correlated image spaces. Highly correlated image spaces between a pair of subjects can imply functional alignment of the subjects. In statistics, canonical correlation analysis (CCA) is used to find the projections of two sets of random variables that are maximally correlated: Given two sets of random variables $Y_1 \in R^N$ and $Y_2 \in R^M$, the aim is to find $z_1 = Y_1 w_1^T$ and $z_2 = Y_2 w_2^T$ such that the following is maximized:

$$\rho = \frac{z_1^T z_2}{\|z_1\| \|z_2\|}.$$

The solution to this problem is given by solving for the largest eigenvalue and the corresponding eigenvector of a generalized eigenvalue problem utilizing self and cross covariance matrices of the two sets of variables. The subsequent pairs of $a_1$ and $a_2$ are found by using eigenvalues of decreasing magnitudes. It is worth noting that the subsequent canonical covariates are orthogonal within and across the datasets.

CCA is extended to handle multiple sets of variables in a variety of ways optimizing for different criterion. These methods are collectively called Generalized Canonicals Correlation Analysis (GCCA) and in our presentation we consider the variant that maximizes the sum of correlations of every pair of datasets. GCCA finds canonical covariates by solving a generalized eigenvalue problem derived from the self and cross covariance matrices. Borrowing from the SRM notation, we can then write the following for each subject:

$$S_i = X_i W_i^T,$$

where $W_i$ is the projection operator from the voxel space to the common response space. Unlike SRM, there is no orthogonality constraint on $W_i$, however the resulting covariates encoded by $S_i$ are orthogonal. We then define the super subject response as follows:

$$S = \sum_{i=1}^{m} S_i.$$

Given the individual shares responses and the super subject, we develop two methods for subsequent learning tasks that leverage data from other subjects. Our motivation stems from the fact that we might only be able to isolate a subset of the activations in each subject reliably; however combined as a super subject, we are able to utilize information from other subjects.

A separate issue with the GDR methods described above is that there is no guarantee that the response variables learned are particularly informative. They explain the brain activation common across subjects, regardless of whether it represents any of the features of interest or something else. In some embodiments, a variant of Shared Response Modeling (referred to herein as supervised SRM or "SSRM") may be applied, which combines the process of learning an SRM with the process of learning a decoder of semantic features of the stimulus (a semantic vector Z as used herein). In doing so, it generates response variables that are particularly suitable for decoding, rather than just to explain all of the brain activation across subjects.

Supervised Shared Response Modeling

When data from multiple subjects are available under the same experimental stimuli, information across samples can be fused to obtain a more refined representation corresponding to the stimuli. This refined representation can be helpful in a discriminative setting such as for classification or in a generative setting. Assume that we have N subjects where each subject's activity matrix is denoted by X, of size $d_i \times m$ where $d_i$ is the number of voxels for subject i and m is the number of experimental concepts. The aim is to find a factorization of $X_i$ as follows:

$$X_i = W_i S$$

$$s.t. \cdot W_i^T W_i = I.$$

In this factorization $W_i$ is of size $d \times r$ and encodes the decomposition of each concept into r orthonormal components. S is of size $r \times d$ and it is shared across the subjects. S and the set of $W_i$'s, $\{W_i\}$, can be found by solving the following optimization problem:

$$\operatorname{argmin}_{W_i, S} \sum_{i=1}^{N} \|X_i - W_i S\|_F^2$$

$$s.t. \; W_i^T W_i = I.$$

The optimization problem given above can be solved by alternating minimization. The shared response can be updated using $S = 1/N \sum_{i=1}^{N} W_i^T X_i$. The update step of $\{W_i\}$ corresponds to computing the polar decomposition of $X_i S^T$ for each subject (i.e., $W_i = U_i V_i^T$ where $X_i S^T = U_i \Sigma_i V_i^T$).

Often the aim in extracting a shared response across subjects is to learn classifiers or generative models corresponding to stimuli. However, these steps are usually independent (i.e., shared response modelling is succeeded by the learning process). Here, we aim to fuse the shared response modeling with the learning process. The joint approach can enhance the overall performance as the shared response modeling is provided with labels that can aid in extracting relevant information from subjects. This approach is referred to herein as Supervised Shared Response Modeling (SSRM).

We briefly review the discriminative setting that we use together with the shared response. Given a description of the experimental stimuli, Z of size $m \times f$ where m is the number of experimental stimuli as used above and f is the number of components used to express the stimuli, the following model can be written as follows:

$$Z = S^T B.$$

In this linear model, B encodes coefficients that map the shared response to each component of the description of the stimuli. In some embodiments, because the stimuli is concerned with semantic representation in the brain, a semantic representation may be used of each concept. Conventionally, given S, B can be learnt in a variety of ways that incorporate some form of regularization for B to avoid over fitting to the training data.

In SSRM shared response modeling and learning may be combined as follows:

$$\text{argmin}_{W_i,S,B}(1-\alpha)\sum_{i=1}^{N}\|X_i - W_iS\|_F^2 + \alpha\|Z - S^TB\|_F^2 + \alpha\beta\|B\|_F^2$$

$$\text{s.t. } W_i^T W_i = I.$$

In SSRM, the relative weights of the response modeling part and learning part are controlled with a parameter $\alpha \in [0,1]$ and B is regularized by penalizing its norm that is controlled by the parameter B. SSRM is optimized by using a two-step alternating procedure that updated S and ($\{W_i\}$, B) pair. Note that the update steps corresponding to the ($\{W_i\}$,B) pair de-couples naturally as they are not paired in a term in the SSRM formulation. S is then updated solving the following normal equations:

$$(N(1-\alpha)I + \alpha BB^T)S = (1-\alpha)\sum_{i=1}^{N}W_i^T X_i + \alpha BZ^T.$$

B is updated by solving the following normal equations:

$(SS^T+\beta 1)B=SZ.$ $\{W_i\}$ is updated using the polar decomposition as mentioned above.

In discriminative learning settings it is customary to add a bias term to the coefficient matrix B to account for different offsets that can occur in test and training datasets. The SSRM framework described herein can include the bias term with a slight modification of the formulation as follows:

$$\text{argmin}_{W_i,S,B,b_0}(1-\alpha)\sum_{i=1}^{N}\|X_i - W_iS\|_F^2 + \alpha\left\|Z - [S^T 1][Bb_0]^T\right\|_F^2 + \alpha\beta\|B\|_F^2$$

$$\text{s.t. } W_i^T W_i = I.$$

In this formulation, $b_0$ is a column vector of bias terms that needs to be learned together with B. The update steps given above are slightly modified to incorporate $b_0$.

Generating Synthetic Brain Images for Training Brain Decoding Systems

In some embodiments, a generative adversarial framework is applied that utilizes the semantic stimuli and their corresponding fMRI images to learn to generate images from semantic stimuli. This can be considered learning to map the distribution of semantic representations to the space of fMRI image distribution.

Figure 4:
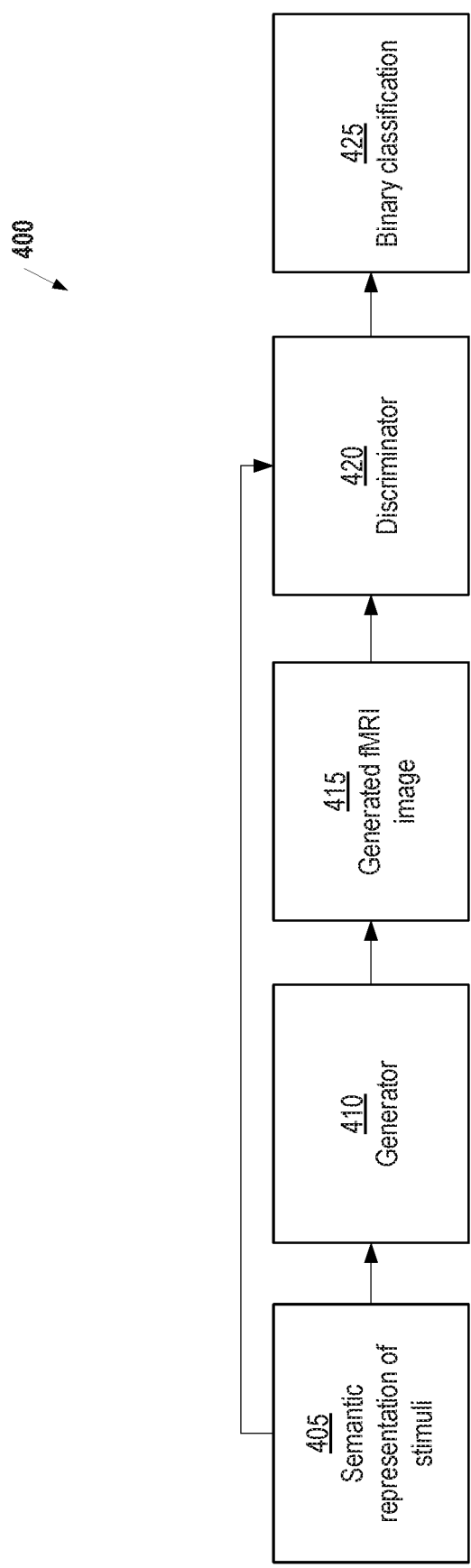
FIG. 4 illustrates an example framework for learning a generative model of semantic representative in the brain, according to some embodiments.

FIG. 4 illustrates an example fMRI Generative Adversarial Network (GAN) framework 400 for learning a generative model of semantic representative in the brain, according to some embodiments. As would be understood by one skilled in the art, a GAN comprises a generative model and a discriminative model (typically implemented using neural networks) that learn to create synthetic data similar to known input data. In this example of FIG. 4, the generator 410 takes the semantic representation of the stimuli 405 as input and then generates an fMRI image 415. Then the discriminator 420 decides whether the generated image looks realistic (i.e., shares similar characteristics with real fMRI images). The aim of the generator 410 is to be able to generate realistic renderings of the brain that can pass the discriminator's 420 test and the discriminator 420 tries to tell the generated images from the real acquisitions. This framework can be trained using techniques generally known in the art. Unlike conventional techniques, the generating process is driven through an implicit cost that stems from the discriminator 420. The discriminator 420 can be optionally provided the corresponding stimuli vector from the semantic representation of the stimuli 405. In this case the discriminator tests if the provided pair is a valid pair.

The framework 400 shown in FIG. 4 confirms that the generated images are similar to real acquisitions; however the framework 400 does not guarantee that the generated images will be consistent with the particular stimuli as the discriminator does not consider such a criterion. The optional semantic representation input to the discriminator has the potential to learn this consistency given a large amount of data but it can be limited when it is hard to obtain a large amount of stimuli-fMRI acquisition pairs.

Figure 5:
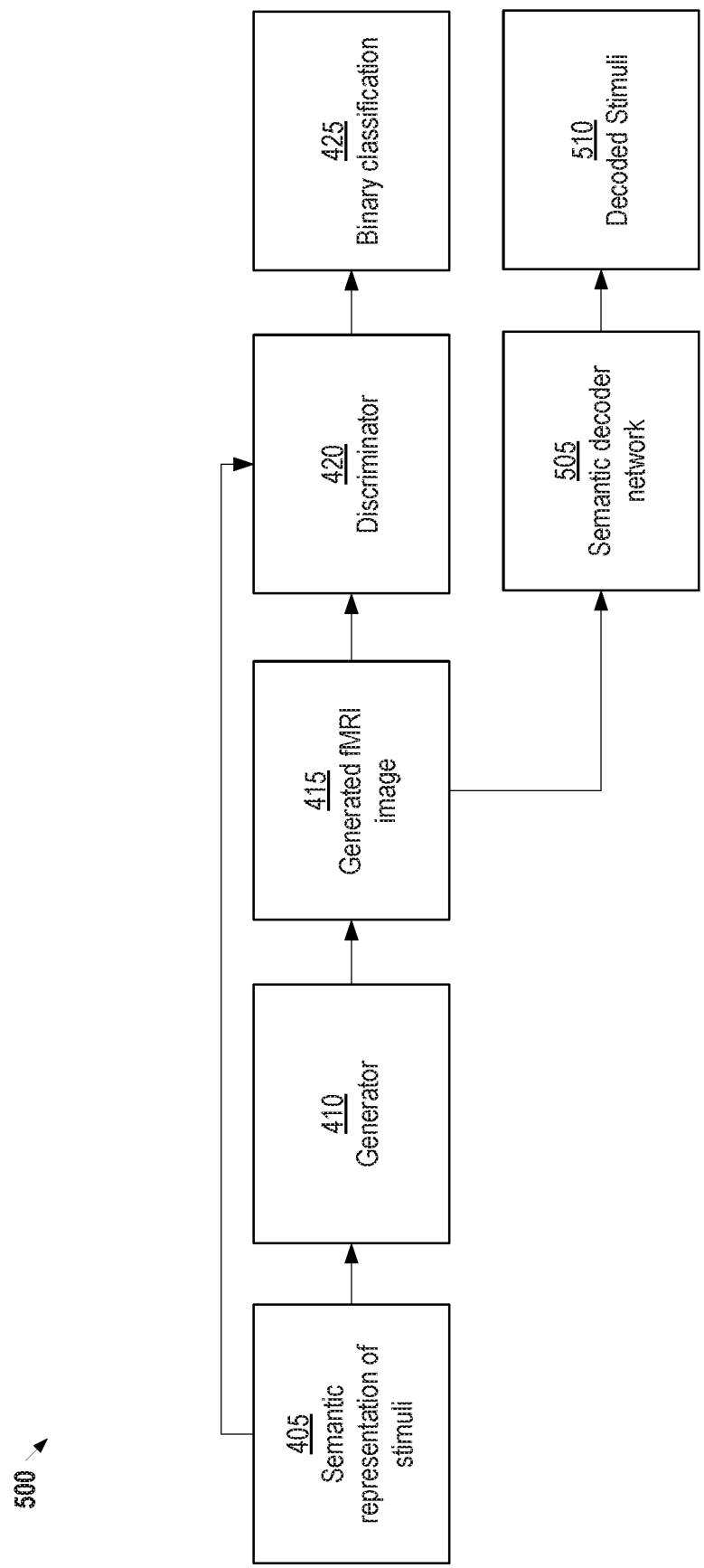
FIG. 5 illustrates a fMRI-GAN coupled with a semantic decoder network, according to some embodiments.

In some embodiments, to address the need to obtain a sufficient amount of stimuli-fMRI acquisition pairs, the framework 400 may be coupled with a semantic decoder network as illustrated in FIG. 5. The semantic decoder network 505 takes the generated fMRI image 415 and generates decoded stimuli 510. The cost associated with the decoded stimuli 510 helps driving the evolution of the generator together with the discriminator 420. That is, generator 410 evolves with gradients back-propagated from both the semantic decoder network 505 and the discriminator 420. The semantic decoder network 505 can be pre-trained or fully trained before integrating it with the framework 400. In the first case, the semantic decoder 505 can be trained within the framework 400 whereas for the latter case, the semantic decoder network 505 can be kept fixed (i.e., not updated).

Figure 6:
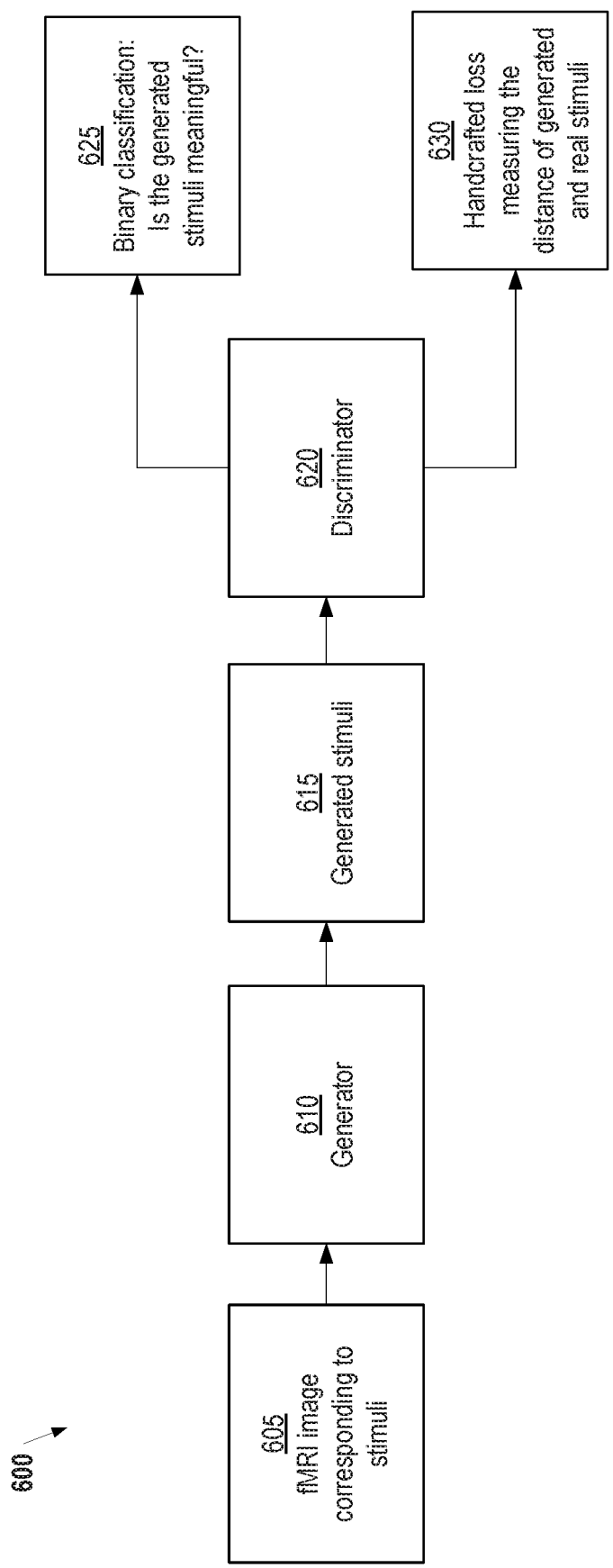
FIG. 6 shows a framework for learning a decoder in an adversarial setting, according to some embodiments.

In other embodiments, a cyclic consistency constraint can be used to enforce to generate fMRI images that are in agreement with the stimuli. In this method, the GAN is used to generate text from a given fMRI image. In principal this is similar to learning a semantic decoder but in an adversarial setting. This is illustrated in FIG. 6. Given an fMRI image corresponding to stimuli 605, a generator 610 generates generated stimuli 615. The discriminator 620 then produces a binary classification 625 indicating whether or not the generated stimuli are meaningful. The adversarial loss can be augmented with a handcrafted loss measuring the distance of the generated and real stimuli 630.

In some embodiments, the networks described above can be connected through a cyclic consistency constraint. The fMRI-GAN achieves the mapping F(S)=I, where S is the input sematic vector and I is the generated input image. The adversarial decoder learns the mapping G(I)=S. The cyclic consistency is then the following constraints: G(F(S))≈S F(G(I))≈I. The first constraint encourages a semantic vector to be mapped back to itself after going through F and G, respectively. The second constraint encourages an input image to be mapped back to itself after going through G and F, respectively. Unlike the first approach, the cyclic approach does not require labeled data (i.e., stimuli-brain image pair but (weak) supervision can be integrated into this framework as well).

The approaches described above for generating synthetic data can be extended to leverage data from multiple subjects. This can be achieved either by extracting shared information using a preprocessing technique such as canonical correlation analysis and its generalizations. Nonetheless, this can be as well achieved using a machine learning technique and can be further coupled with the frameworks described above.

Direct Mapping Between Brain Images and Stimulus Representations

Figure 7:
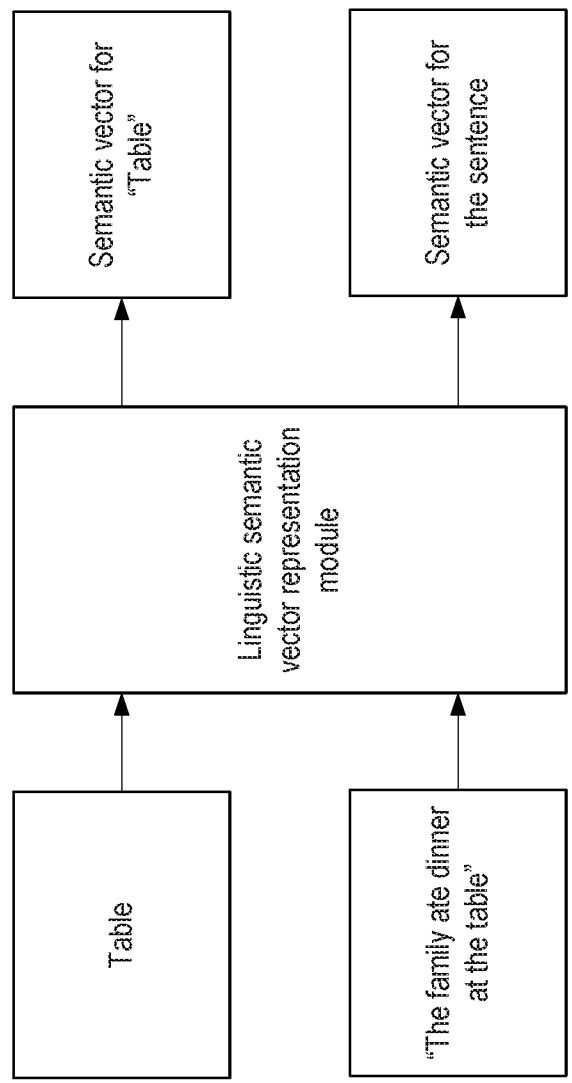
FIG. 7 shows a module for assigning a semantic vector to words, phrases or sentences used as stimuli in the system training data, according to some embodiments.
Figure 8:
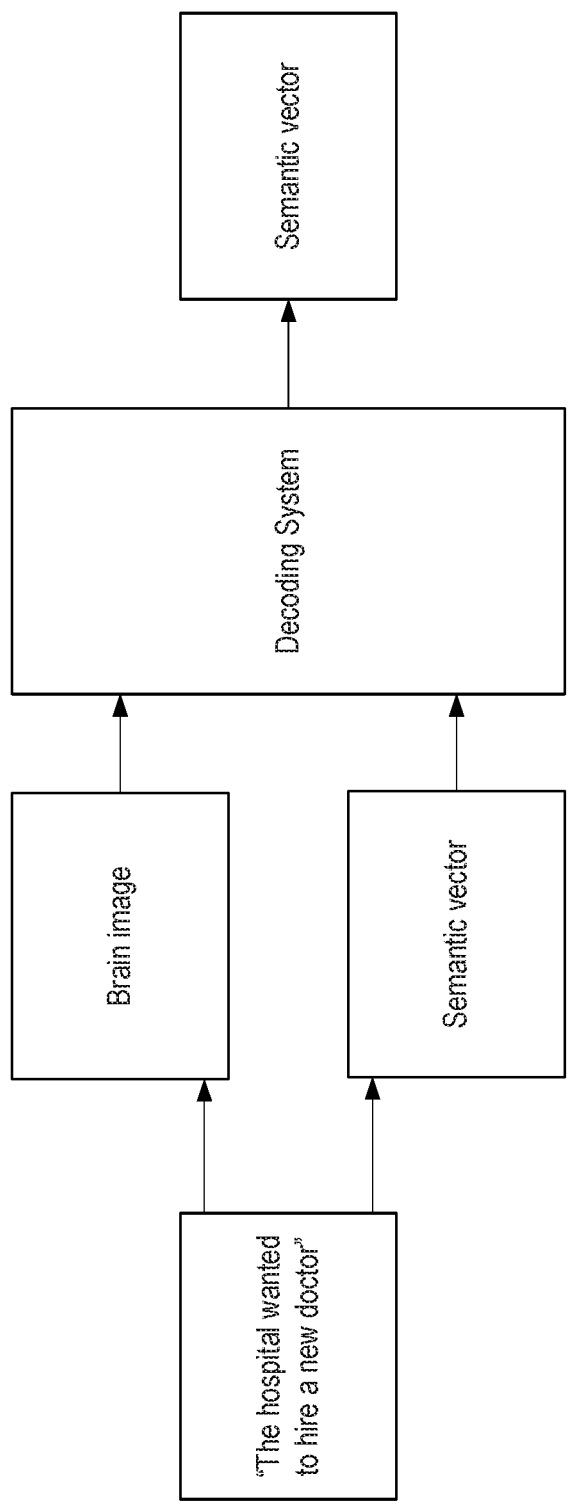
FIG. 8 illustrates a generic decoding of semantic vector from functional images, according to some embodiments.

State-of-the-art fMRI experiments often use complex stimuli, with the ultimate goal being to identify what in the brain activation encodes characteristics of those stimuli (e.g., visual, semantic, etc.). The underlying assumption is that semantic content can be represented as a vector in a semantic space as shown in FIG. 7. More specifically, FIG. 7 shows a module for assigning a semantic vector to words, phrases or sentences used as stimuli in the system training data, according to some embodiments. In this context, "decoding" means being able to infer what that semantic space representation would be for the semantic content present in a particular brain image. This is often done by learning a mapping that associates the presence of each characteristic with its effect on the pattern of brain activation across voxels. This is then used to decode those features from new brain imaging data as shown in FIG. 8.

Recent studies also reported reconstructions of the spatial structure of natural images, while simultaneously revealing their semantic content. The reconstruction of a natural image here was defined as the image that had the highest posterior probability of having evoked the measured response. To include the semantic information in the model, it was also necessary to annotate the semantic category of training set images by human observers.

In some embodiments of the present invention, a system is used for decoding from multi-modality brain imaging data and directly mapping to any form of stimulus representations. The decoding system described has several advantages compared to the current decoding techniques. First, it is unnecessary to quantify the content of the system input/ output. Secondly, the system monitors the mental state of a patient under any condition. Third, the system output is in a form that can be understood by human (natural language, pictures, movies, sounds, etc.). Fourth, the system output can be adapted according to the working condition.

A very large neuroimaging dataset is a prerequisite for designing a system that can directly map brain images to stimulus representations. This dataset should preferably include functional brain images from any modality and corresponding stimuli that elicit the brain activation. The stimuli can be any format of communication (e.g., reading texts, listening stories, watching movies) via different modalities of sense (e.g., visual, auditory, olfactory).

Figure 9:
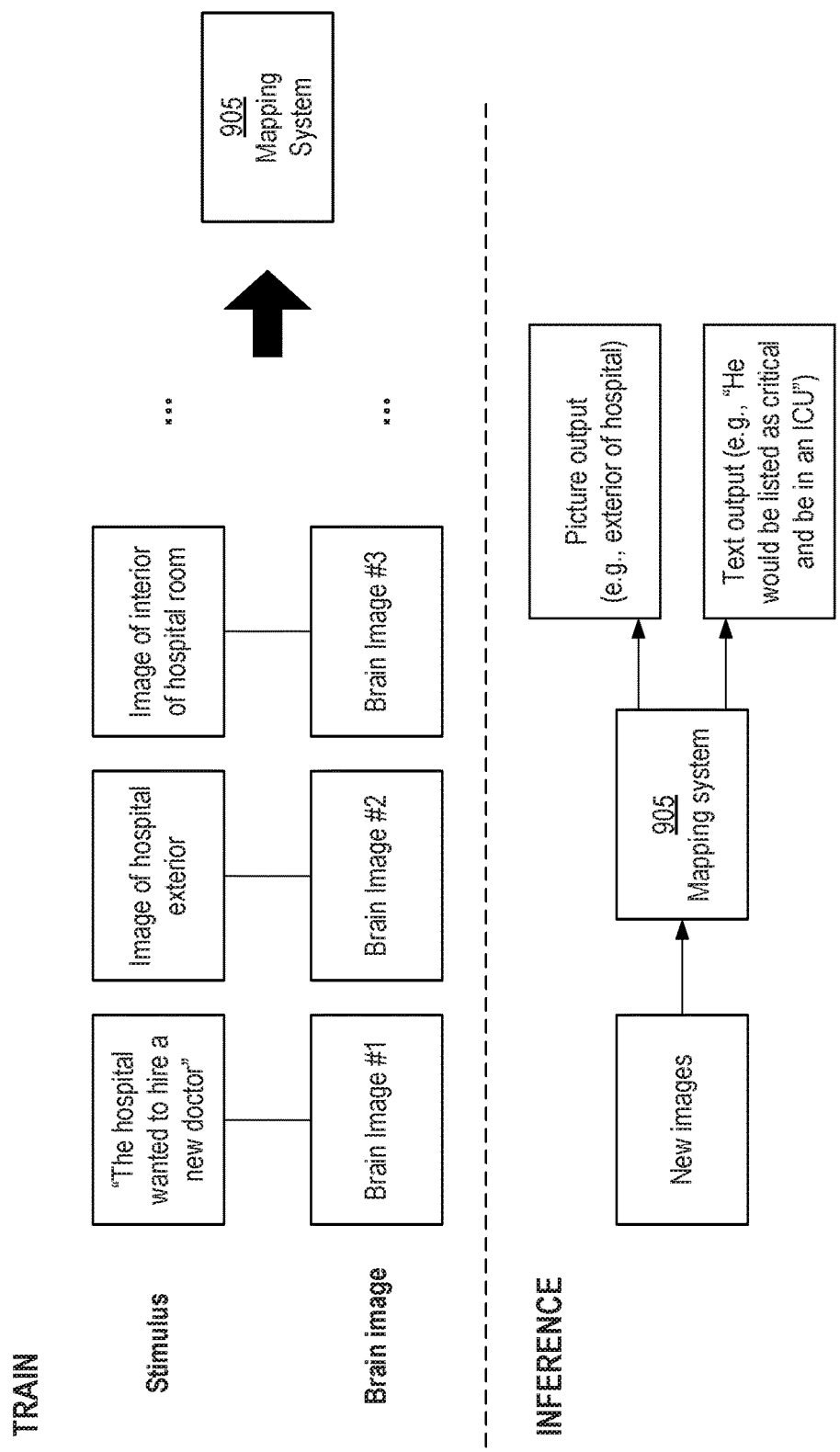
FIG. 9 provides a high-level overview of the mapping system, as it may be implemented in some embodiments of the present invention.

FIG. 9 provides a high-level overview of the mapping system, as it may be implemented in some embodiments of the present invention. During the training phase the mapping system 905 is presented with a series of brain images (brain image #1, brain image #2, etc.) and the stimuli used to generate the brain images. For example, the mapping system 905 is presented with the text "the hospital wanted to hire a new doctor" and an fMRI image of the resulting brain activity (i.e., brain image #1). During the inference phase, new images are presented to the mapping system 905 and the system 905 outputs a picture output (e.g., exterior of a hospital) or textual output (e.g., "he would be listed as critical and be in an ICU.").

Because it is impossible to acquire enough paired data and stimulus from one subject, it is necessary to have a technique that is able to integrate data acquired from multiple subjects and multiple sessions. The mapping system described herein uses GDR. In the GDR setting the aim is to achieve functional alignment of stimuli responses in distinct subjects assuming that the stimuli invoke similar functional responses. In essence, GDR maps the activation across the subject's voxels to a new space that is shared between the subjects. The other way of enriching the dataset is to utilize synthetic data as described in the previous section.

Assuming we have already obtained enough paired data, the mapping module can be trained based on a Recurrent Neural Network such as a long short-term memory (LSTM). One possible embodiment of the system shows subjects sentences while functional brain images are acquired, and then trains the Recurrent Neural Network to produce the sequence of words in each sentence given the corresponding brain image.

Figure 10:
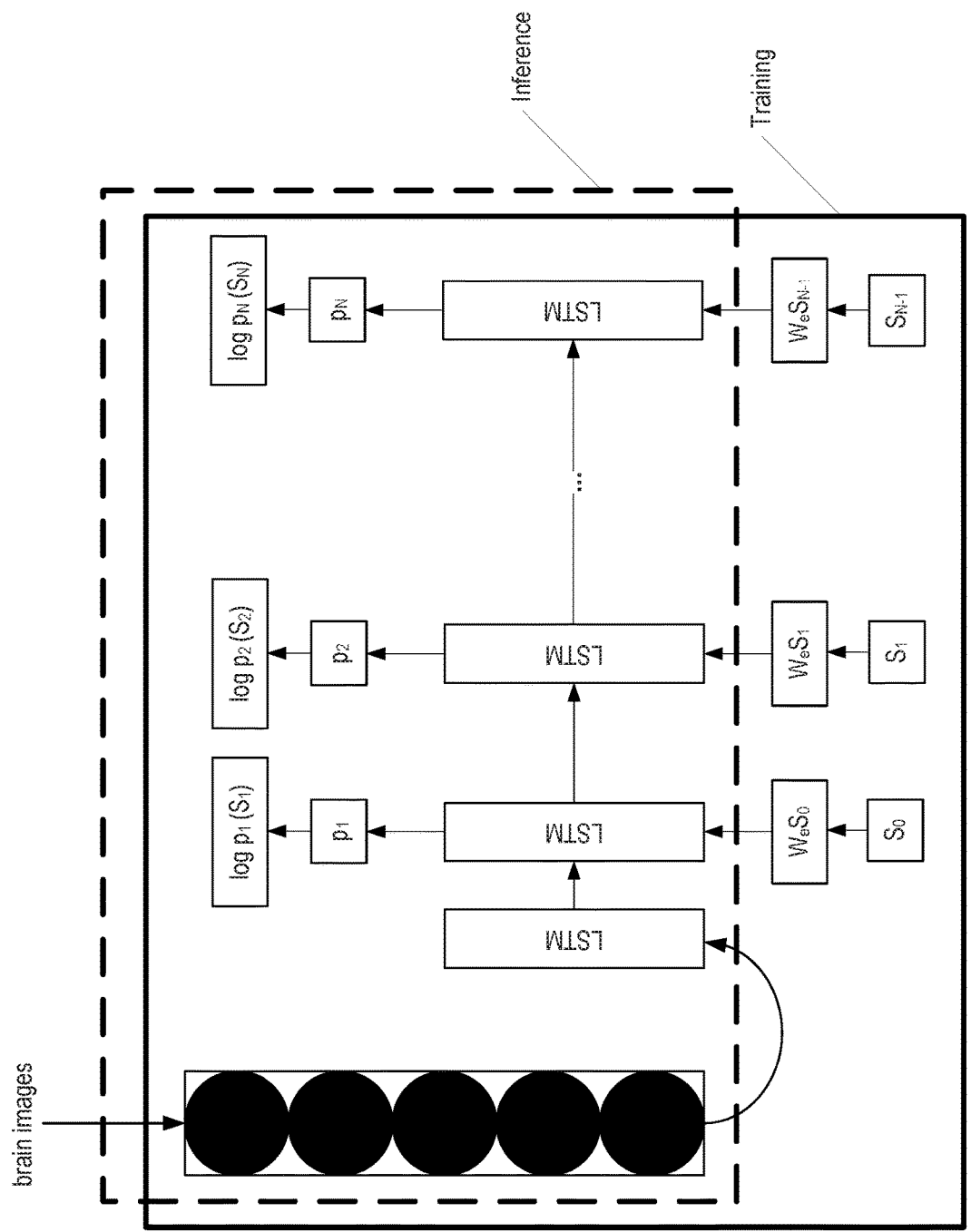
FIG. 10 shows a recurrent neural network that can be used to implement the mapping system illustrated in FIG. 9.

For training, the model receives input of size N derived from some text corpus D in the form of pairs $<s\_i, v\_i>$, where $v\_i$ is a brain activation pattern evoked by stimulus $s\_i$. Note here $s\_i$ could be a segment of text, a short movie clip, a piece of music etc. The parameters theta of the model are estimated so that given the vector $v\_i$, the reconstruction of the stimulus $s\_i$ is as accurate as possible, as measured with a cross-entropy criterion. During inference, the model receives a new brain activation pattern $v\_j$ and produces a certain type of stimulus forming the prediction for the current brain image $v\_j$. FIG. 10 shows a recurrent neural network that can be used to implement the mapping system illustrated in FIG. 9. In this example, the solid line represents the training procedure and the dashed line represents the inference procedure.

Figure 11:
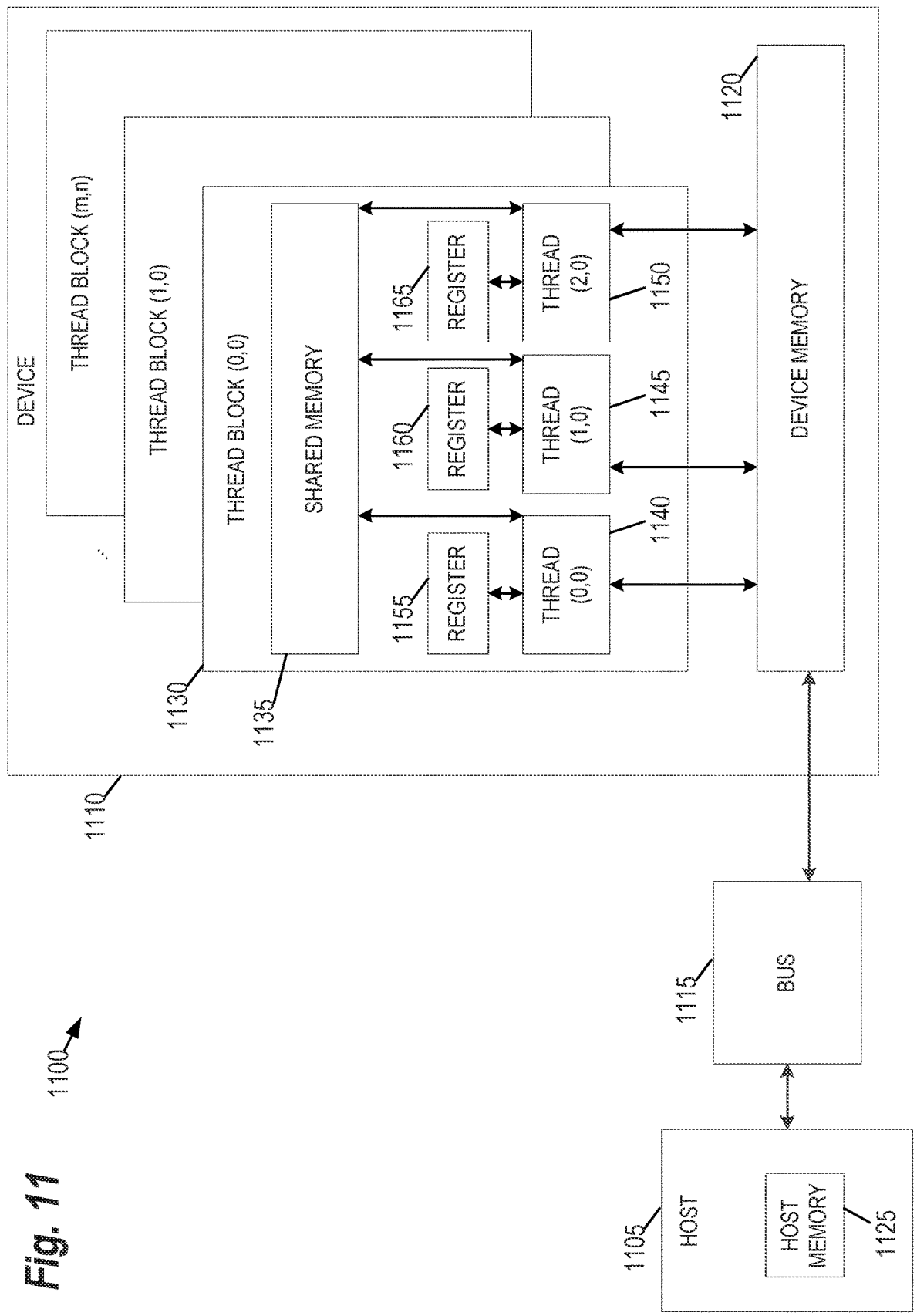
FIG. 11 provides an example of a parallel processing platform that may be utilized to implement the machine learning models and other aspects of the various workflows discussed herein.

FIG. 11 provides an example of a parallel processing platform 1100 that may be utilized to implement the machine learning models and other aspects of the various workflows discussed herein. This platform 1100 may be used in embodiments of the present invention where NVIDIA CUDA™ (or a similar parallel computing platform) is used. The architecture includes a host computing unit ("host") 1105 and a graphics processing unit (GPU) device ("device") 1110 connected via a bus 1115 (e.g., a PCIe bus). The host 1105 includes the central processing unit, or "CPU" (not shown in FIG. 11), and host memory 1125 accessible to the CPU. The device 1110 includes the graphics processing unit (GPU) and its associated memory 1120, referred to herein as device memory. The device memory 1120 may include various types of memory, each optimized for different memory usages. For example, in some embodiments, the device memory includes global memory, constant memory, and texture memory.

Parallel portions of a big data platform and/or big simulation platform may be executed on the platform 1100 as "device kernels" or simply "kernels." A kernel comprises parameterized code configured to perform a particular function. The parallel computing platform is configured to execute these kernels in an optimal manner across the platform 1100 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the platform 1100 of FIG. 11 (or similar architectures) may be used to parallelize portions of the model based operations performed in training or utilizing the smart editing processes discussed herein. For example, in embodiments where a convolutional neural network is used as the machine learning model, the platform 1100 can be used to perform operations such as forward and backward convolution, pooling, normalization, etc. Additionally, the parallel processing platform 1100 may be used to execute multiple instances of a machine learning model in parallel. For example, multiple instances of the machine learning models may be executed in parallel with different parameters.

The device 1110 includes one or more thread blocks 1130 which represent the computation unit of the device 1110. The term thread block refers to a group of threads that can cooperate via shared memory and synchronize their execution to coordinate memory accesses. For example, in FIG. 11, threads 1140, 1145 and 1150 operate in thread block 1130 and access shared memory 1135. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 11, the thread blocks 1130 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 11, registers 1155, 1160, and 1165 represent the fast memory available to thread block 1130. Each register is only accessible by a single thread. Thus, for example, register 1155 may only be accessed by thread 1140. Conversely, shared memory is allocated per thread block, so all threads in the block have access to the same shared memory. Thus, shared memory 1135 is designed to be accessed, in parallel, by each thread 1140, 1145, and 1150 in thread block 1130. Threads can access data in shared memory 1135 loaded from device memory 1120 by other threads within the same thread block (e.g., thread block 1130). The device memory 1120 is accessed by all blocks of the grid and may be implemented using, for example, Dynamic Random-Access Memory (DRAM).

Each thread can have one or more levels of memory access. For example, in the platform 1100 of FIG. 11, each thread may have three levels of memory access. First, each thread 1140, 1145, 1150, can read and write to its corresponding registers 1155, 1160, and 1165. Registers provide the fastest memory access to threads because there are no synchronization issues and the register is generally located close to a multiprocessor executing the thread. Second, each thread 1140, 1145, 1150 in thread block 1130, may read and write data to the shared memory 1135 corresponding to that block 1130. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 1110 to read and/or write to the device memory. Device memory requires the longest time to access because access must be synchronized across the thread blocks operating on the device. Thus, in some embodiments, each fMRI dataset can be divided into segments using data locality techniques generally known in the art. Then, each segment can be processed in parallel using register memory, with shared and device memory only being used as necessary to combine the results to provide the results for the complete dataset.

The embodiments of the present disclosure may be implemented with any combination of hardware and software. For example, aside from parallel processing architecture presented in FIG. 11, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A system for decoding brain imaging data of individual subjects by using additional imaging data from other subjects, the system comprising:
a functional Magnetic Resonance Imaging (fMRI) scanner configured to acquire an fMRI dataset corresponding to a subject, wherein the fMRI dataset comprises brain activation patterns resulting from presentation of a plurality of stimuli to the subject;
one or more processors configured to:
apply a group dimensionality reduction (G.D.R.) technique to the fMRI dataset to transform it into a low-dimensional space of response variables shared by a plurality of subjects, and
apply a machine learning model to the transformed fMRI dataset to predict one or more target variables comprising one or more semantic vectors describing the plurality of stimuli,
wherein at least a portion of the fMRI dataset comprises a synthetic dataset, and the one or more processors are further configured to:
generate the synthetic dataset using a GAN framework comprising a generator and a discriminator connected using a cyclic consistency constraint that minimizes difference between the plurality of stimuli and generated stimuli produced by the generator.

2. A computer-implemented method for decoding from brain imaging data of individual subjects by using additional imaging data from other subjects, the method comprising:
receiving a plurality of functional Magnetic Resonance Imaging (fMRI) datasets corresponding to a plurality of subjects, wherein (a) each fMRI dataset corresponds to a distinct subject and (b) each fMRI dataset comprises brain activation patterns resulting from presentation of a plurality of stimuli to the distinct subject; and
performing a supervised Shared Response Modelling (SSRM) to (i) apply a group dimensionality reduction (G.D.R.) technique to the plurality of fMRI datasets to yield a low-dimensional space of response variables shared by the plurality of subjects and (ii) train a model to predict a set of target variables based on the low-dimensional space of response variables, wherein the set of target variables comprises one or more semantic vectors describing the plurality of stimuli,
wherein at least a portion of the plurality of fMRI datasets comprise synthetic datasets and the method further comprises:
generating the synthetic datasets using a Generative Adversarial Network (GAN) framework comprising a generator, a discriminator, and a semantic decoder network, wherein the generator evolves with gradients back-propagated from the semantic decoder network and the discriminator.

3. The method of claim 2, further comprising:
receiving a new fMRI dataset corresponding to a new subject;
applying the SSRM technique to transform the new fMRI dataset into new response variables in the low-dimensional space; and
applying the model to the new response variables to predict one or more target variables.

4. The method of claim 2, wherein the set of target variables further comprise a visual representation of one or more stimuli included in the plurality of stimuli.

5. The method of claim 2, wherein the model comprises a Recurrent Neural Network.

6. A computer-implemented method for decoding from brain imaging data of individual subjects by using additional imaging data from other subjects, the method comprising:
receiving a first set of functional Magnetic Resonance Imaging (fMRI) datasets corresponding to a plurality of subjects, wherein (a) each fMRI dataset corresponds to a distinct subject; (b) each fMRI dataset comprises brain activation patterns resulting from presentation of a plurality of stimuli to the distinct subject, (c) each fMRI data is in voxel space;
applying a group dimensionality reduction (G.D.R.) technique to the first set of fMRI datasets to yield a low-dimensional space of response variables shared by the plurality of subjects;
generating a second set of fMRI datasets corresponding to the plurality of subjects by projecting the low-dimensional space of response variables back to voxel space;
training a model to predict a set of target variables based on the second set of fMRI datasets, wherein the set of target variables comprise one or more semantic vectors describing the plurality of stimuli.

7. The method of claim 6, further comprising:
receiving a first new fMRI dataset corresponding to a new subject in voxel space;
applying the G.D.R. technique to transform the first new fMRI dataset into new response variables in the low-dimensional space;
generating a second new fMRI dataset by projecting the low-dimensional space of the new response variables back to voxel space; and
applying the model to the second new fMRI dataset to predict one or more target variables.

8. The method of claim 6, wherein the target variables further comprise a visual representation of one or more stimuli included in the plurality of stimuli.

9. The method of claim 6, wherein at least a portion of the first set of fMRI datasets comprise synthetic datasets and the method further comprises:
generating the synthetic datasets using a Generative Adversarial Network (GAN) framework comprising a generator, a discriminator, and a semantic decoder network, wherein the generator evolves with gradients back-propagated from the semantic decoder network and the discriminator.

10. The method of claim 6, wherein at least a portion of the first set of fMRI datasets comprise synthetic datasets and the method further comprises:
generating the synthetic datasets using a GAN framework comprising a generator and a discriminator connected using a cyclic consistency constraint that minimizes a difference between the plurality of stimuli and generated stimuli produced by the generator.

11. The method of claim 6, wherein the model comprises a Recurrent Neural Network.

* * * * *